United States Patent [19]
Hahn et al.

[11] Patent Number: 5,490,810
[45] Date of Patent: Feb. 13, 1996

[54] PROCESS AND DEVICE FOR MANUFACTURING A STRUCTURAL PART, ESPECIALLY OF A CERAMIC TOOTH RESTORATION, AND A PROCESS OF MAKING SONOTRODE CROWNS

[75] Inventors: Rainer Hahn, Rottenburg; Bernd Burger, Alling, both of Germany

[73] Assignee: Thera Patent GmbH & Co. KG Gesellschaft Für Industrielle Schutzrechte, Seefeld, Germany

[21] Appl. No.: 126,208

[22] Filed: Sep. 24, 1993

[30] Foreign Application Priority Data

Sep. 24, 1992 [DE] Germany ............ 42 32 023.3

[51] Int. Cl.⁶ .................................................. B24B 1/00
[52] U.S. Cl. ............... 451/165; 451/28; 451/54; 264/16; 264/19
[58] Field of Search .................... 451/1, 11, 14, 451/28, 54, 55, 56, 59, 162, 164, 165; 264/16, 19

[56] References Cited

U.S. PATENT DOCUMENTS

| | | |
|---|---|---|
| 3,971,133 | 7/1976 | Mushabac . |
| 4,343,111 | 10/1982 | Inoue ..................................... 451/165 |
| 4,616,447 | 10/1986 | Haas et al. .............................. 451/165 |
| 4,734,173 | 3/1988 | Walter et al. . |
| 4,751,916 | 6/1988 | Bory . |
| 4,838,786 | 6/1989 | Reher et al. ............................ 433/9 |
| 4,904,348 | 2/1990 | Domes et al. . |
| 4,961,782 | 10/1990 | Reher et al. ............................ 451/165 |
| 4,973,357 | 11/1990 | Reher et al. ............................ 451/165 |
| 5,095,602 | 3/1992 | Reher et al. ............................ 451/165 |
| 4,216,583 | 3/1994 | Reynolds ................................ 433/9 |

FOREIGN PATENT DOCUMENTS

| | | |
|---|---|---|
| 2326956 | 12/1974 | Germany . |
| 3617790A1 | 1/1987 | Germany . |
| 4029285A1 | 3/1992 | Germany . |

OTHER PUBLICATIONS

"Keramikbearbeitung" (Working of Ceramics, Carl Hansen Verlag, Munchen 1989 (pp. 423–443)).

Primary Examiner—Maurina T. Rachuba
Attorney, Agent, or Firm—Foley & Lardner

[57] ABSTRACT

In a process and apparatus for the overall machining of a ceramic tooth restoration and producing of appropriate sonotrode crowns, these sonotrode crowns act on a workpiece one after the other, however from the same direction in space and are activated by the same ultrasonic transmitter. For the production of said sonotrode crowns, a geometrical model corresponding to the ultrasonic machining apparatus is used.

17 Claims, 6 Drawing Sheets

PROCESS AND DEVICE FOR MANUFACTURING A STRUCTURAL PART, ESPECIALLY OF A CERAMIC TOOTH RESTORATION, AND A PROCESS OF MAKING SONOTRODE CROWNS

BACKGROUND OF THE INVENTION

The present invention relates to ultrasonic working of workpieces for making structural parts, especially for producing ceramic tooth crowns, as, for example, dental veneers, inlays, crowns or bridges from dental ceramic material. Due to their favourable biological-chemical properties, their high tissue-tolerance and their low tendency for plaque-accumulation, ceramic tooth replacement materials are generally discussed as being material systems of top quality.

More specifically, the invention relates to a process of producing a ceramic tooth restoration by ultrasonic machining apparatus in which a receiver for a profiled sonotrode crown is positioned on each side of the workpiece to be worked, the receiver being in opposing relation to one another, and wherein in a first machining step, the workpiece is held by a workpiece holder, a first sonotrode crown is activated and one of the workpiece halves is machined to the desired shape by bringing the first said sonotrode crown into form-fitting engagement with said workpiece, and wherein in a second machining step the workpiece is held by the sonotrode crown by the form-fitting engagement, and a second sonotrode crown is activated for machining the remaining half of the workpiece to the desired shape. The invention also relates to an ultrasonic machining apparatus for carrying out the process.

The process as above described and the ultrasonic machining device for carrying out the process are known from DE 39 28 684 C2 (HAHN)(corresponding to U.S. application Ser. No. 07/678,367). Particular reference is additionally made to this patent publication and the prior art named therein.

Further, the publication "Keramikbearbeitung" (Working of Ceramics), Carl Hanser Verlag, München 1989, pages 423–443 discloses a process and a device for working brittle materials, e.g. ceramic, glass, glass-ceramics etc., with the aid of ultrasound. The mechanical energy of the oscillating tool is transferred to a lapping mixture in a working gap between the sonotrode crown and the tool, which leads to a formation of chip and finally to a projection of the sonotrode crown in the workpiece. However, these methods are restricted to the forming of one workpiece surface. The necessary shaping tools are made by conventional metal-cutting methods, e.g. turning on a lathe, milling, drilling, etc., or by electrical discharge machining. Moreover, geometrically complex shapes of small dimensions frequently cannot be made from conventional workpiece materials.

DE 40 29 285 A1 (SIEMENS) describes a sonotrode having its shaping part, i.e. its sonotrode crown, made at least partially from silicon. This choice of material serves to optimise the wear behavior. It furthermore facilitates the use of the so-called microstructure technique (Mikrostruktur-technik) for forming the working surface of the sonotrode crown. The microstructure technique is known from the field of manufacture of semiconductor elements and comprises, for example, photolithography and isotropic and anisotropic etching methods.

The above-mentioned electrical discharge machining process for making structural parts for the working of dental prostheses is known, for example, from DE 37 35 558 C2 (HERAEUS) and DE 35 44 123 C2 (WALTER). The disadvantages thereof have been discussed in the above-mentioned DE 39 28 648 C2 (HAHN).

Due to the unavoidable and partly significant wear and the short tool life of the sonotrode crowns resulting therefrom, conventional precise mechanical or microelectronic manufacturing processes or manufacturing processes by electrical discharge machining are not economical for the making of sonotrode crowns.

Finally, DE 36 06 305 A1 (HANSEN) describes an ultrasonic machining tool comprising an ultrasonic generator (ultrasonic converter including amplifier) and a sonotrode. The sonotrode is fixedly clamped to the ultrasonic generator by a differential screw and centered by cylindrical shoulders. The sonotrode can thereby easily be substituted without necessitating a new adjustment of the workpiece.

SUMMARY OF THE INVENTION

The present invention provides a new process of ultrasonically making a structural part, particularly of a ceramic tooth restoration, and a corresponding ultrasonic machining apparatus; further, a process and an apparatus suitable therefor for making sonotrode crowns for use in the above process and for use in the above ultrasonic machining apparatus.

These objects are met in accordance with the first embodiment of the invention by, between the two machining steps, exchanging the first sonotrode crown with the second sonotrode crown attached to the opposing receiver and aligning both sonotrode crowns with respect to one another for continuing the machining of said workpiece, with the workpiece being held in form-fitting engagement or again being brought into form-fitting engagement with the first sonotrode crown.

In accordance with a modified form by the invention, a disposable model of the structural part is produced, a plastically deformable and hardening or curable material is deposited on the disposable model, and the sonotrode crowns are produced by directly molding them from the disposable model. In this method, the body formed by curing of the curable substance is separated along the equatorial line of the disposable model and the two body parts thus obtained are each worked to form complete sonotrode crowns.

The subject matter according to the invention improves the manufacture of small-lot production series significantly. Particularly, it enables an especially economical, less cost- and time-intensive manufacture of this kind of series. Only a single ultrasonic sound producing unit is needed for overall working of the workpiece without necessitating a re-adjustment in connection with any necessary change of the sonotrode crown. The modified form of the invention is based on the principles of the model and articulation technique and enables the production of exactly fitting complementary sonotrode crowns for overall machining of dental ceramic blanks.

A further feature of the invention is that the free edges of the sonotrode crowns correspond to the equatorial line of the tooth crown. This has a advantage of the particularly simple exact adjustment of the two sonotrodes with respect to one another, namely by detecting a form-fitting between the two sonotrode crown edges.

The further of the invention resides in providing two equal, preferably identical, devices for holding the sonotrode which, significantly facilitates interchangeability without needing a re-adjustment.

The variants of the mechanical partition the ultrasonic generator and sonotrode crown-holding device lead to a further simplification of the fitting interchangeablility of the sonotrode crown holding device. The term "ultrasonic generator" in this context refers to the actual generator, including any necessary amplifiers. This does not exclude the possibility that further amplifiers may be provided in the sonotrode itself.

The coupling of the sonotrode with the ultrasonic amplifier is per se known from DE 36 06 305 (HANSEN) or the corresponding U.S. Pat. No. 4,751,916. The additional threaded connection includes the threaded connection described in these two documents.

Means are provided at the end of the device adjacent to the ultrasonic generator for receiving and adjusting of the means supporting the sonotrode crowns, enabling the supporting engagement of the first sonotrode crown with the workpiece during a second working step. Adjustment means are provided permitting a convenient and exact positioning of the two sonotrode crowns with respect to one another.

The method includes the per se known functional reconstruction of the tool restoration to be formed (e.g. inlay, veneer, partial crown, crown, bridge etc.) from a thermoplastic modelling material, e.g. moulding wax.

The curable substance specified in claim 14 can be a known moulding wax or a polymer material.

The equatorial line defines the so-called model equator, for instance the tooth crown equator measured by the largest diameter of the model, related to the model longitudinal axis or the virtual working axis. This limitation guarantees that so-called "working shadows" are not formed during the cutting of the sonotrode crown into the workpiece. The model equator defines the plane, oriented essentially traverse to the longitudinal axis of the model, from which the outer surfaces of the tooth restoration are surrounded by monotonically or strictly monotonically tapered sections of the restoration. Therefore, the body formed by curing of the moulding substance is separated along the equatorial line of the disposable model.

A further feature of the invention is the provision of a key-lock which serves a later positionally exact adjustment of the two sonotrodes with respect to one another.

According to a further aspect of the invention a so-called "wax-up" may stay on the model base normally provided by a dental laboratory and will be adjusted releasably on one model sonotrode. Imaginarily, the "wax-up", in other words the model form, is separated into two "halves" along the prosthetical equator. Initially, the "occlusal" half of the restoration is covered with a low shrinking, fast curing polymer up to the equator and is fixedly aligned in the restorational axis to a prefabricated secondary sonotrode. After termination of the process steps, the wax model is carefully taken out of the sonotrode crown forms achieved by moulding.

The step of casting of the crown hollow form with liquid metal serves to optimise wear resistance of the sonotrode crowns by transforming the polymer sonotrode crowns into metal. The transforming occurs according to a casting process known in the dental field. Manual finishing of the sonotrode crowns is not necessary In order to avoid the forming of burrs during subsequent ultrasonic machining with the sonotrode crowns, the manufacturing process may be carried out so that their free edge zones overlap in a scissor-fashion.

According to a further advantageous embodiment, the sonotrode crown is soldered, welded or glued to the adjacent sonotrode part.

The geometrical model in accordance with the invention ensures a mutual fitting adjustment of the sonotrode crown at maximum degrees of freedom for aligning of the sonotrode parts adjacent to the sonotrode crowns and further ensures sufficient working space for manual activity during the manufacture of the sonotrode crowns. In the following, the invention will be further described with reference to embodiments shown schematically in the attached drawings.

DESCRIPTION OF THE PREFERRED EMBODIMENTS

Figure 1:
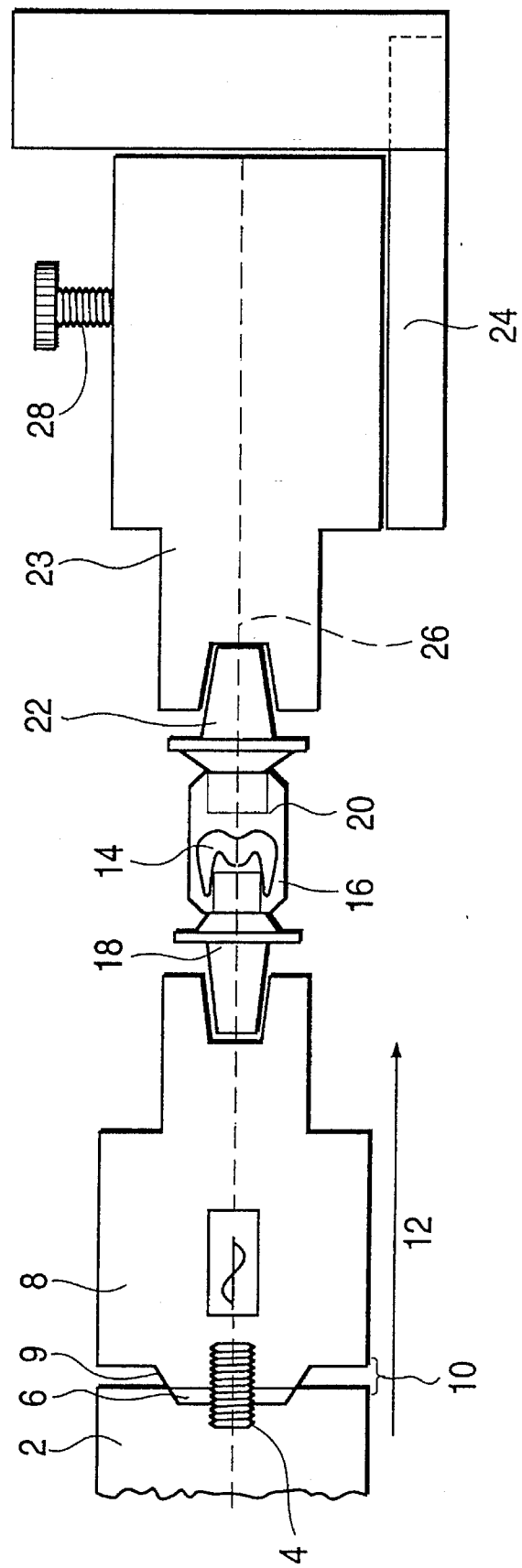
FIG. 1 shows a longitudinal sectional view of a partial section of an ultrasonic machining device.

The embodiment shown in FIG. 1 comprises an ultrasonic generator 2, which is mechanically coupled to a primary sonotrode 8 by means of a fixing screw 4 and a centering cone 6 with a shoulder, the sonotrode 8 including a conical flange 9 corresponding to the centering cone 6. In the following, the ultrasonic generator 2 and the primary sonotrode 8 are referred to as "ultrasonic transmitting device" 10. The ultrasonic transmitting device 10 is advanced in a known manner using an advancing control 12 toward the workpiece 14 to be machined, which in the present case is a dental ceramic workpiece 14, such that the machining gap between the active sonotrode crown 16 and the workpiece surface has the desired dimensions. A secondary sonotrode 18 serves as a device for supporting the sonotrode crown 16, is formed to be conical at its end adjacent to the primary sonotrode 8 and is centered by a corresponding centering cone at the end of the primary sonotrode 8 facing the workpiece.

The secondary sonotrode 18 serves to support the sonotrode crown 16. The sonotrode crown 16 can be pressed, soldered, welded and/or glued to it, or it can be attached by any other known joining means.

The dental ceramic workpiece 14 is held in form-fitting engagement with a further passive sonotrode crown 20 at its side opposing the active sonotrode crown 16. FIG. 1 therefore illustrates the second working step mentioned in the introductory part of the description.

The passive sonotrode crown 20 is also positioned on a secondary sonotrode 22, which is formed like the opposing secondary sonotrode 18. Specifically, it has the same conical centering flange which is inserted in a corresponding centering cone of a receiving member 23. The identical form of the devices for supporting the sonotrode crowns 16, 20, (in the present case the secondary sonotrodes 18, 22) allows a simple exchange of the two secondary sonotrodes 18, 22 in the primary sonotrode 8.

The correct alignment of the two sonotrode crowns 16, 20 is achieved by a key, i.e. by at least one form-fitting location at their free edges. This form fit can be controlled by taking the workpiece 14 out of its working position, bringing said sonotrode crowns 16, 20 into form-fitting relation with one another and inserting them into the centering cone 6 into this alignment. Subsequently, the workpiece 14 is brought into form-fitting relation with the passive sonotrode crown 20 again, and the active sonotrode crown 16 is advanced in the forward direction towards said workpiece 14.

Alternatively, a position-locking key of the sonotrode crowns can be provided by a groove and tongue arrangement in said centering cone 6 and the conical flanges for the secondary sonotrode(s) 18, 22.

The receiving member 23 for the passive sonotrode crown 20 is supported by two adjusting shafts or rods 24 which are aligned parallel to the advancing direction, i.e. the machining axis 26. If the workpiece 14 and the sonotrode crowns 16, 20 are arranged in their machining position, the receiving member 23 is fixed by a fixing screw 28.

The dental ceramic tooth restoration is finished as soon as the free edges of the sonotrode crowns 16, 20 meet one another. The tooth restoration is punched by the sonotrode crowns 16, 20 by machining from both sides in two subsequent machining steps. The tooth restoration is always machined from one and the same direction in space, namely from the direction in which the ultrasonic transmitting device 10 is arranged.

In order to prevent the formation of burrs, the free ends of the edges of the sonotrode crowns 16, 20 overlap in a scissor-fashion.

Figure 2:
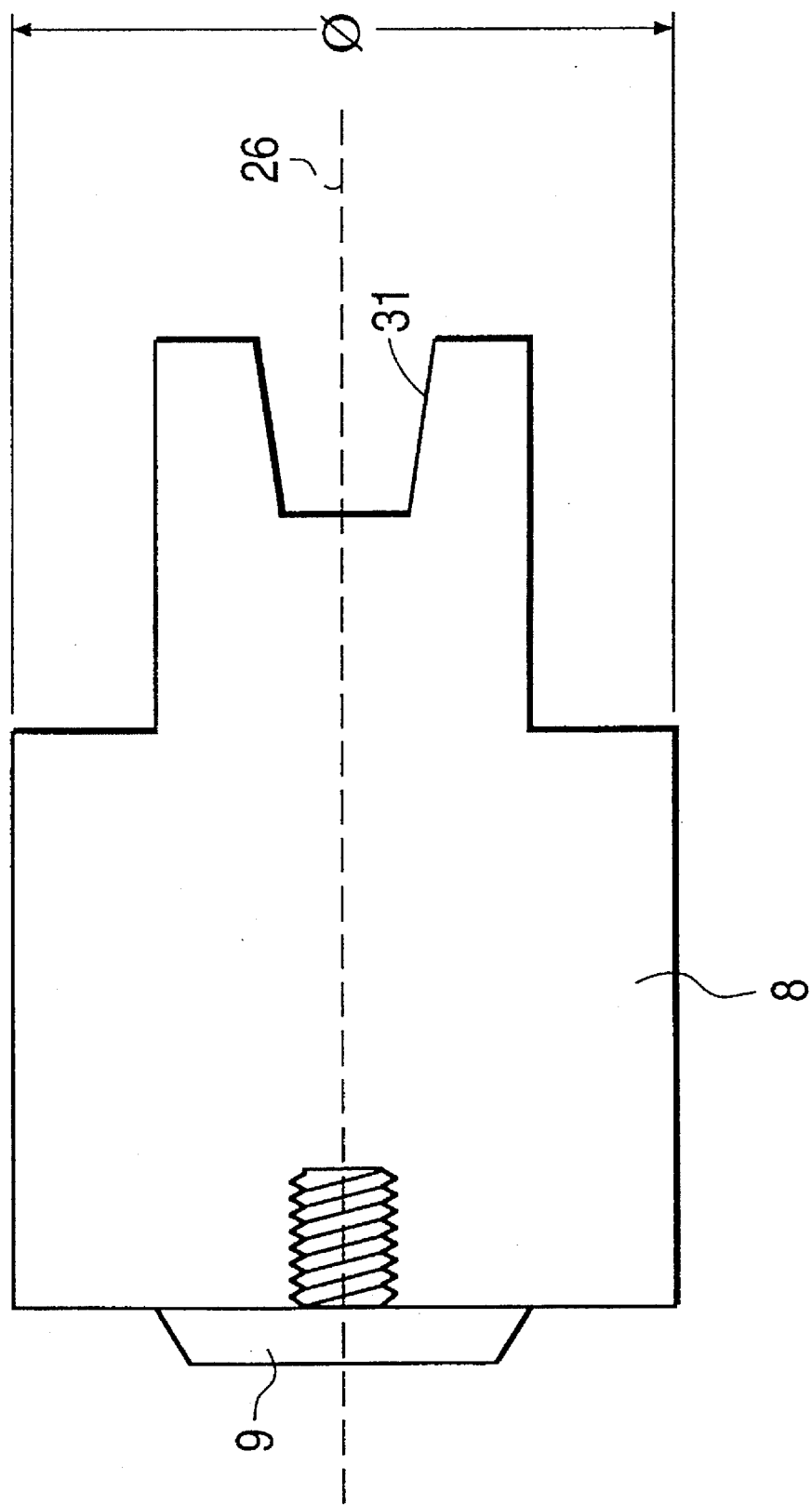
FIG. 2 shows an enlarged view of the primary sonotrode of FIG. 1.

FIG. 2 shows the primary sonotrode 8 in enlarged perspective. It is characterised by a centering conical flange 9 facing the generator and a conical flange 31 facing the workpiece. Preferably, the primary sonotrode 8 has a regular cylindrical outer wall with a diameter which is equal to the diameter of the receiving member 23, and a position key with the centering cone 6 of the ultrasonic generator 2, especially of the groove and tongue key type.

According to a further embodiment not shown in the drawings, it is the primary sonotrode 8 which serves as an exchangeable device for supporting the sonotrode crown 16. The secondary sonotrode 18 is in this case not necessary. Instead, the receiving member supporting the passive sonotrode crown 20 is also shaped as primary sonotrode 8.

Figure 3:
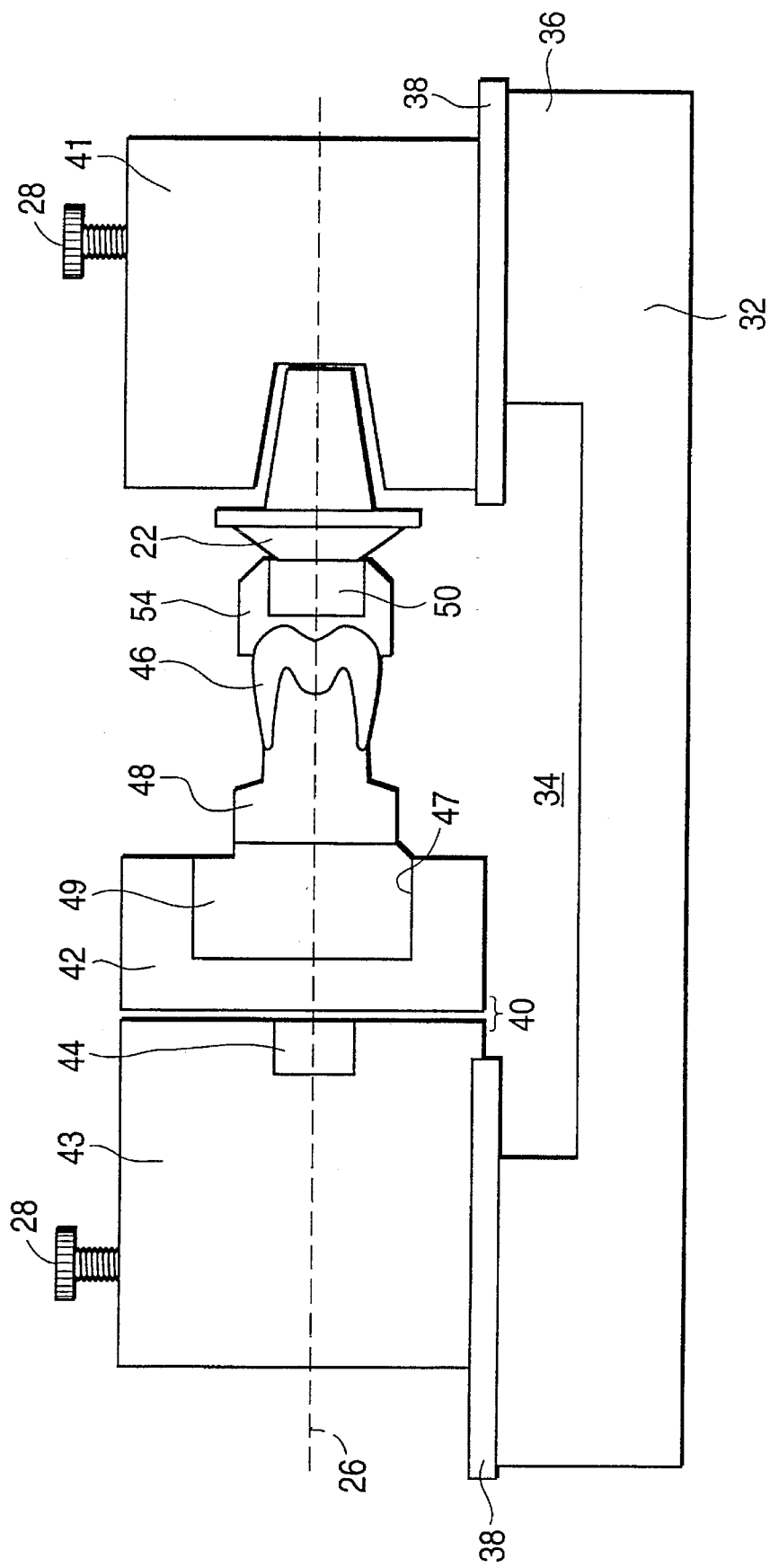
FIG. 3 shows an apparatus for making sonotrode crowns by a geometrical model of an ultrasonic machining device and a process step of the making of sonotrode crowns.

The geometrical model of an ultrasonic machining apparatus shown in FIG. 3 serves to make two sonotrode crowns which are complementary to one another for overall machining of a ceramic tooth restoration, in the present case a crown. The geometrical model comprises a base plate 32, shown in a longitudinal sectional view in FIG. 3, i.e. in a vertical sectional view, the sectional plane of which contains the machining longitudinal axis 26. The cross section of the base plate 32 corresponds to the section shown in FIG. 5 by another embodiment of a geometrical model. As is shown in these sectional views, two intersecting trough-shaped recesses 34 and 37 are formed in the base plate 32 such that column-shaped protrusions 36 protrude at the four corners of the base plate 32 in an upward direction. The column-shaped protrusions 36 have a rectangular cross-sectional shape in a horizontal sectional view.

A guiding rod 38 is provided on each column-shaped protrusion 36 which projects beyond said column-shaped protrusion 36 on both sides. Altogether, four guiding rods 38 are provided. All guiding rods 38 are aligned in parallel to the machining axis 26. They support, in pairs, a receiving member 40, 41. Each receiving member 40, 41 is shiftable on the guiding rods 38 in the direction of the machining axis 26 and can be positioned in any position on the guiding rods 38 by fixing screws 28 or by tension brackets or other means.

The receiving member 40 shown in the left part of FIG. 3 comprises a section 42 facing the workpiece which can be shifted in a plane which is orthogonal to the machining axis 26. This section 42 is therefore shiftable in all three space dimensions; thus, it is shiftable to a maximum extent. It can be connected to the section 43 being fixable on the guiding rods 38 by a cross support. In the present embodiment it is fixed by magnetic supports 44 and is therefore moveable in the orthogonal plane particularly easily. A magnet may be provided such as a permanent magnet or—to allow changing the magnetic force—an electromagnet with a controllable current supply. The shiftable section 42 projects over the trough-shaped groove or recess 34 and is therefore easily accessible. The wax model ("wax-up") 46 supplied from the dental laboratory together with a model base 48 is fixed by putty material in a recess 47 of the shiftable receiving member 42. The putty 49 facilitates the alignment of the wax model 46—its prosthetical equatorial plane must be aligned with the machining longitudinal axis 26. The prosthetical equator is preferably determined in the dental laboratory and drawn on the "wax-up" 46. Its positional alignment is thereby facilitated.

After aligning the wax model 46 in the machining position, i.e. in the position in which the tooth restoration is, so to speak, "punched" by the sonotrode crowns at a later stage, the occlusal surface is coated with a low-shrinking, fast-curing polymer up to the equatorial line, in other words, it is directly moulded. The polymer layer is then aggregated until it reaches a crown-facing cone 50 and is fixed therewith. The crown-facing section of the secondary sonotrode 22, called the sonotrode head, may have a thread instead of the cone 50. The secondary sonotrode 22 may further have a different form of retention for the sonotrode crown.

A sonotrode crown 54 manufactured in this way usually cannot yet be used for ultrasonic machining of a brittle hard material. In this case, it is transferred to a metal casting mould. Up to the transfer into the metal mould, it constitutes a presonotrode 54.—The secondary sonotrode 22 may also be referred to as a "semifinished secondary sonotrode", whereby the term "secondary sonotrode" refers to covering all of the semifinished secondary sonotrodes and secondary sonotrode crowns.

After the presonotrode 54 has been attached to the secondary sonotrode 22, the wax model 46 adheres exactly to the cured sonotrode crown surface.

The free edge surfaces of the presonotrode crown 54 ending at the equatorial line are now isolated and the model base 48 is carefully removed. Now a second "cervical" sonotrode crown is built up instead of the model base 48 in generally the same manner as the occlusal presonotrode crown 54. For this, a second secondary sonotrode is arranged in the shiftable receiving section 42 of the left receiving member 40, analogously to the first secondary sonotrode 22.

The cervical presonotrode crown is attached to the corresponding secondary sonotrode in the same manner as the occlusal presonotrode crown 54. Preferably, the same materials are used for making the second presonotrode crown as for the first presonotrode crown 54. The presonotrode crowns may be fixed to their corresponding secondary sonotrode heads at the same time as the moulding process or afterwards.

Subsequently, the "wax-up" 46 is carefully removed, for example by infusing in hot water—which may be done before or after the separation of the presonotrodes along the isolated equatorial line.

For optimising the wear behaviour of the sonotrode crowns, the sonotrodes including the attached sonotrode crowns are embedded in a refractory mould. The crowns are then removed, for example by burning out. The cavity thus formed is then poured out with metal. In this way, wear-resistant sonotrode crowns are directly cast with the head of the secondary sonotrodes. The sonotrode head carrying the sonotrode crown is retentively shaped in a suitable manner, for example by forming a reversed cone or by the above-mentioned thread. The joining may be optimised by additional soldering, welding or gluing of the joints.

A further possibility consists in the conical forming of the already-mentioned secondary sonotrode heat, which enables a removal of the sonotrode crown after curing. The sonotrode crowns are exactly repositionable through the conical head of the secondary sonotrode and can now be pressed, glued, soldered and/or welded by conventional bonding methods.

As already mentioned, the subsequent ultrasonic machining is carried out in two successive steps. First of all, the first sonotrode crown is completely moulded using a suitable lapping suspension in a blank made of dental ceramics. Afterwards, the moulded blank is held by the first sonotrode crown and is machined by the second sonotrode crown from the contralateral side. The intrusion depth is limited by contact of the corresponding sonotrode crowns. A so-called "ultrasonic punching" of the desired structured part is achieved, wherein scissor-like overlapping edge regions of the sonotrode crowns inhibits the forming of burrs.

Figure 4:
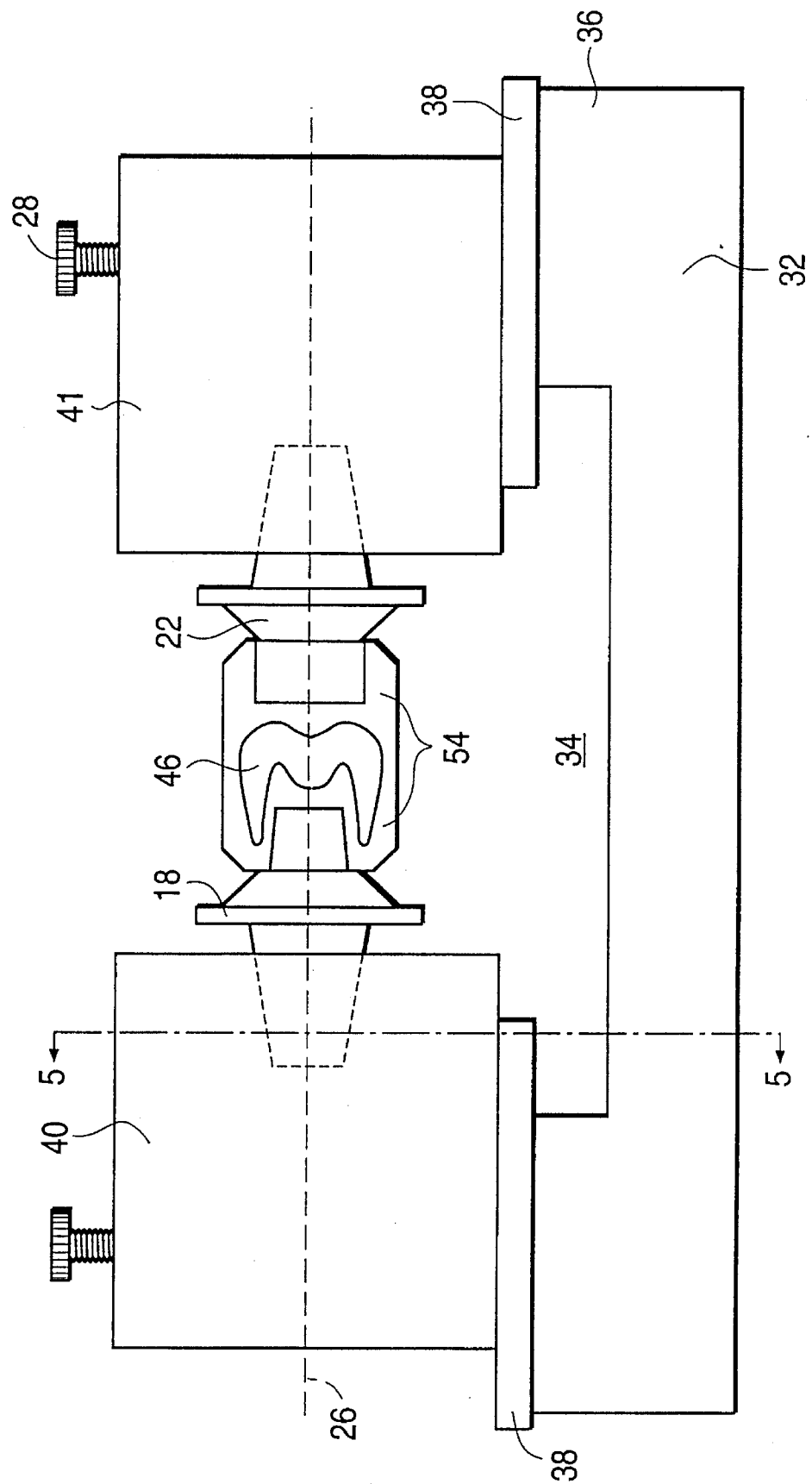
FIG. 4 shows a further geometrical model of an ultrasonic machining device for making sonotrode crowns and a further process step of the making of sonotrode crowns.

A further embodiment of an apparatus for making of two complementary sonotrode crowns 54 according to the invention is shown in FIG. 4—however in a different state of machining as the embodiment of FIG. 3.

The two sonotrode crowns 54 are already fixed on the corresponding secondary sonotrodes or semifinished sonotrodes 18, 22. Only the wax model 46 must be removed and the two sonotrode crowns 54 must be separated from one another. The step of casting-on of the sonotrode crowns 54 in the mentioned refractory mould is still to follow. In this embodiment, in a first process step the wax model 46 has been releasably fixed directly by the putty material 49 to the secondary sonotrode 18.

Figure 5:
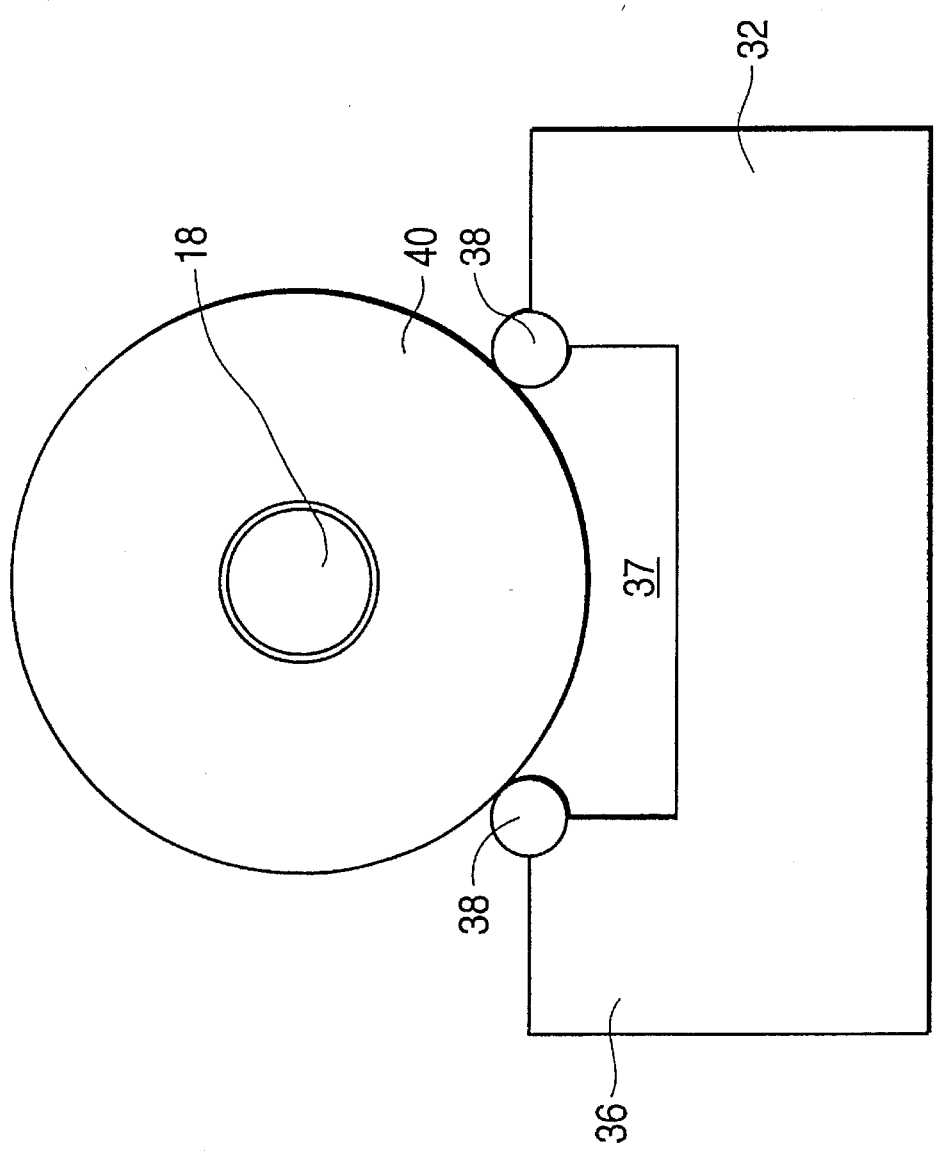
FIG. 5 shows a sectional view along the line A—A in FIG. 4.

The vertical cross sectioned view in FIG. 5 along the line A—A of FIG. 4 shows a regular cylindrical receiving member 40 which lies on the likewise circular cylindrical guiding rods 38 under line contact.

Figure 6:
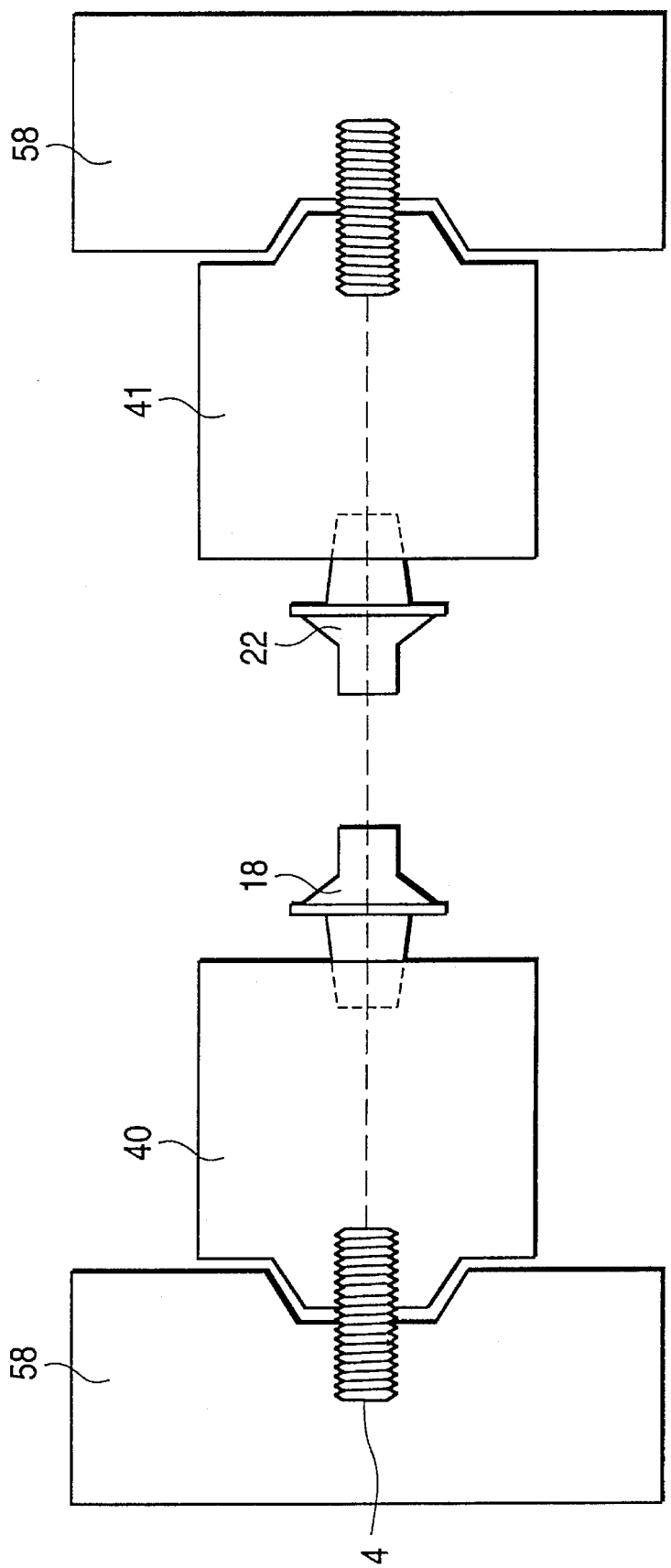
FIG. 6 shows a further geometrical model of an ultrasonic machining device for making crowns.

FIG. 6 finally shows a further embodiment of a geometrical model of an ultrasonic machining device for making sonotrodes which are complementary to each other.

In this embodiment, receiving members 40, 41 are attached in exactly the same way to two fixed supports 58 facing each other, just as the primary sonotrode 8 in the ultrasonic generator 2 of FIG. 1.

A primary sonotrode 8 may also be used directly as a receiving member 40 in the geometrical model.

We claim:

1. Process of machining a workpiece by means of an ultrasonic machining apparatus, in which a receiver for a profiled sonotrode crown is positioned on each side of the workpiece to be worked, the receiver being in opposing relation to one another, comprising (a) in a first machining step, holding said workpiece by a workpiece holder activating a first sonotrode crown through its receiver and machining one of the workpiece halves to the desired shape, said sonotrode crown thereby being brought into form-fitting engagement with said workpiece; and (b) in a second machining step, holding said workpiece by said first, now passive, sonotrode crown by means of said form-fitting engagement, activating a second sonotrode crown and machining the remaining half of the workpiece to the desired shape, characterised in that (c) between said two machining steps
 (c1) said first sonotrode crown is exchanged with said second sonotrode crown and attached to the opposing receiver;
 (c2) both sonotrode crowns are aligned with respect to one another for continuing the machining of said workpiece;
 (c3) wherein said workpiece is held in said form-fitting engagement or is again brought into said form-fitting engagement with said first sonotrode crown.

2. The process of claim 1 for producing a tooth crown or the like, wherein sonotrode crowns are used whose free edges correspond to the equatorial line of the tooth crown and wherein said sonotrode crowns are aligned with respect to one another between the two machining steps by form fitting of their free edges.

3. The process of claim 1, wherein said sonotrode crowns machine said workpiece generally in a horizontal direction.

4. An ultrasonic machining apparatus for machining a workpiece having a first side and a second side, the apparatus having a machining axis and including:

(a) an oscillating means for generating ultrasonic oscillations;

(b) an attaching means opposing said oscillating means and aligned with said oscillating means with respect to said machining axis;

(c) a first sonotrode crown;

(d) a second sonotrode crown;

(e) a first holding means for holding said first sonotrode crown and being adapted for attachment to said oscillating means for transferring ultrasonic oscillations to said workpiece during machining of said first side thereof and for attachment to said attaching means during machining of said second side of the workpiece;

(f) a second holding means for holding said second sonotrode crown and being adapted for attachment to said oscillating means for transferring ultrasonic oscillations to said workpiece during machining of said second side thereof and for attachment to said attaching means during machining of said first side of the workpiece; and (g) means for advancing an active one of said first and said second sonotrode crowns along said machining axis for machining.

5. The apparatus of claim 4, wherein said first and second holding means have substantially the same shape.

6. The apparatus of claim 4, wherein said oscillating means is arranged on only one side of the workpiece during machining.

7. The apparatus of claim 4, wherein said oscillating means comprises an ultrasonic generator with an attached primary sonotrode and wherein said holding means comprise secondary sonotrodes which are attachable to said primary sonotrode.

8. The apparatus of claim 7, wherein said primary sonotrode has a workpiece facing end and a centering cone at said workpiece facing end, and said secondary sonotrode comprises a conical flange corresponding to the centering cone of said primary sonotrode at an end opposing said workpiece.

9. The apparatus of claim 4, wherein said oscillating means comprises an ultrasonic transmitting device including an ultrasonic generator and a primary sonotrode and said holding means comprise secondary sonotrodes which are directly attachable to said ultrasonic transmitting device.

10. The apparatus of claim 4, wherein each of said first and second holding means includes a centering cone for mechanically coupling said oscillating means thereto.

11. The apparatus of claim 6, wherein means are provided for receiving and adjusting one of said holding means at the end of the apparatus opposing said oscillating means.

12. The apparatus of claim 11, wherein said receiving/adjusting means include two adjusting shafts or rods which are aligned parallel to the machining axis.

13. The apparatus of claim 12, wherein at least the surface of the sonotrode contacting the receiving/adjusting means is formed as a regular cylinder.

14. The apparatus of claim 4, wherein each of said first and second holding means includes a threaded connection for mechanical coupling to said oscillating means.

15. The apparatus of claim 13, wherein the primary and secondary sonotrodes are formed as a regular cylinder.

16. An apparatus for machining a workpiece along a machining axis comprising:
   (a) an ultrasonic generator;
   (b) a first sonotrode crown contacting a first side of said workpiece;
   (c) a first sonotrode holding said first sonotrode crown and transferring ultrasonic oscillations from said generator to said workpiece during machining of the first side thereof;
   (d) a second sonotrode crown contacting a second side of said workpiece;
   (e) a second sonotrode holding said second sonotrode crown and transferring ultrasonic oscillations from said generator to said workpiece during machining of the second side thereof.

17. The apparatus of claim 16, further comprising a sonotrode receiver aligned on said machining axis on an opposite side of said workpiece from said generator, wherein said first sonotrode is attached to said receiver during machining of the second side of the workpiece and said second sonotrode is attached to said receiver during machining of the first side of the workpiece.

* * * * *